United States Patent [19]
Allen et al.

[11] Patent Number: 6,120,798
[45] Date of Patent: Sep. 19, 2000

[54] LIPOSOME-ENTRAPPED POLYNUCLEOTIDE COMPOSITION AND METHOD

[75] Inventors: Theresa M. Allen; Darrin D. Stuart, both of Edmonton, Canada

[73] Assignee: Alza Corporation, Mountain View, Calif.

[21] Appl. No.: 09/103,341

[22] Filed: Jun. 23, 1998

Related U.S. Application Data

[60] Provisional application No. 60/050,490, Jun. 23, 1997.

[51] Int. Cl.$^7$ .......................... A61K 9/127; A61K 48/00; C12N 15/85
[52] U.S. Cl. .......................... 424/450; 514/44; 435/458; 536/23.1; 536/24.5
[58] Field of Search .......................... 424/450; 514/44; 436/13; 435/458, 69.1; 536/23.1, 24.5

[56] References Cited

U.S. PATENT DOCUMENTS

| | | | |
|---|---|---|---|
| 4,394,448 | 7/1983 | Szoka, Jr. et al. | 435/458 |
| 5,705,385 | 1/1998 | Bally et al. | 430/320.1 |

FOREIGN PATENT DOCUMENTS

| | | |
|---|---|---|
| WO 96/40964 | 12/1996 | WIPO . |
| 97/04748 | 2/1997 | WIPO . |
| WO 97/07784 | 3/1997 | WIPO . |

OTHER PUBLICATIONS

Hara, T. et al., "Receptor–mediated transfer of pSV2CAT DNA to a human hepatoblastoma cell line HepG2 using asialofetunin–labeled cationic liposomes," *Gene.* 159: 167–174 (1995).

Hong, K. et al., "Stabilization of cationic liposome–plasmid DNA complexes by polyamines and poly(ethylene glycol)–phospholipid conjugates for efficient in vivo gene delivery," *FEBS.* 400: 233–237 (1997).

"Clinical Protocols," Cancer Gene Therapy 1(4): 289–295 (1994).

Bennett, C.F., et al., "Pharmokinetics in mice of a [$^3$H] labeled phosphorothioate oligonucleotide formulated in the presence and absence of a cationic lipid," Journal of Controlled Release 41:121–130 (1996).

Bligh, E.G., and W.J. Dyer, "A Rapid Method of Total Lipid Extraction and Purification," Can J. Biochem. Physiol. 37(8): 911–917 (1959).

Branch, Andrea D., "A Hitchhiker's Guide to Antisense and Nonantisense Biochemical Pathways," Hepatology 24:1517–1529 (1996).

Juliano, R.L., and Saghir Akhtar, "Liposomes as a Drug Delivery System for Antisense Nucleotides," Antisense Reseach and Development 2:165–176 (1992).

Litsinger, David C., et al., "Fate of cationic liposomes and their complex with oligonucleotide in vivo," Biochimica et Biophysica Acta 1281:139–149 (1996).

Reimer, Dorothy L., et al., "Formation of Novel Hydrophobic Complexes between Cationic Lipids and Plasmid DNA," Biochemistry 34(39): 12877–12883 (1995).

Ropert, C., et al., "Inhibition of the Friend Retrovirus by Antisense Oligonucleotides Encapsulated in Liposomes Mechanism of Action," Pharmaceutical Research 10(10): 1428–1433 (1993).

Szoka, Francis, and Demetrios Papahadjopoulos, "Procedure for preparation of liposomes with large internal aqueous space and high capture by reverse–phase evaporation," Proc. Natl. Acad. Sci. USA 75(9): 4194–4198 (1978).

Wong, M.P., et al., "Catonic Lipid Binding to DNA: Characterization of Complex Formation," Biochemistry 35:5756–5763 (1996).

Zelphati, Oliver and Francis C. Szoka Jr., "Liposomes as a carrier for intracellular delivery of antisense oligonucleotides: a real of magic bullet?" Journal of Controlled Release 41:99–119 (1996).

Zelphati, Oliver, et al., "Synthesis and anti–HIV activity of thiocholesteryl–coupled phosphodiester antisense oligonucleotide incorporated into immunoliposomes," Antiviral Research 25:13–25 (1994).

*Primary Examiner*—David Guzo
*Assistant Examiner*—Jon Shuman
*Attorney, Agent, or Firm*—Judy M. Mohr; Paul B. Simboli; Iota Pi Law Group

[57] ABSTRACT

A liposome composition for administration of a polynucleotide and a method of preparing the composition are described. The liposomes in the suspension are composed predominantly of liposomes having a bilayer membrane formed of cationic vesicle-forming lipids and neutral vesicle forming lipids. The polynucleotide is entrapped in the central core of the liposomes and is localized predominantly on the inner surface of the core.

22 Claims, 8 Drawing Sheets

LIPOSOME-ENTRAPPED POLYNUCLEOTIDE COMPOSITION AND METHOD

This application claims the priority of U.S. provisional application No. 60/050,490, filed Jun. 23, 1997, which is incorporated herein by reference.

FIELD OF THE INVENTION

The present invention relates to a liposome composition having a polynucleotide entrapped therein, and to a method of preparing the liposome composition.

BACKGROUND OF THE INVENTION

In recent years polynucleotides have been studied as possible therapeutic agents due to their ability to alter expression of specific genes. Gene therapy to add a gene function which is missing or absent and to inhibit expression of a gene are under investigation. In particular, gene therapy with antisense oligonucleotides is being widely studied. Oligonucleotides are composed of a string of nucleotide residues complementary to the mRNA of a target gene for hybridizing by Watson-Crick base pairing. In this way, inhibition of translation is achieved, often by mechanisms such as activation of RNAse H or by prevention of the assembly or the progress of the translational machinery (Branch, A. D., *Hepatology* 24(6):1517–1529 (1996)).

One problem with the use of polynucleotides, DNA, RNA and oligonucleotides, as therapeutic agents is a relatively poor ability to cross the cell membrane in order to reach their site of action in the cytoplasm. Polynucleotides carry a negative charge and, therefore, do not readily cross the cell membrane in free form.

Another problem is that polynucleotides can interact with a variety of extracellular molecules which can alter the polynucleotide's bioavailability. Further, polynucleotides are susceptible to degradation in biological fluids and they display pharmacokinetics which may not be favorable for some therapeutic applications.

One approach to overcoming these problems is to administer the polynucleotide in the presence of a lipid vesicle, such as a liposome, and various liposome-based compositions have been proposed (Zelphati, O., and Szoka, F. C., *J. Control. Res.* 41:99–119 (1996)). For example, one proposed composition consists of a polynucleotide mixed with pre-formed cationic liposomes. Such liposomes are generally prepared from a cationic lipid mixed with an approximately equimolar concentration of a membrane destabilizing lipid and/or a neutral lipid, such as dioleoylphosphatidylethanolamine (DOPE). The polynucleotide is mixed with the pre-formed cationic liposomes to form polynucleotide-liposome complexes through electrostatic charge interactions. Such complexes have some in vitro ability to mediate cellular uptake of polynucleotides, however, the relatively large size (200–2000 nm) and poor stability make them unsuitable for in vivo applications, in particular for delivery to organs other than the liver and the lungs (Bennet, C. F., et al., *J. Control. Rel.* 41:121–130 (1996); Litzinger, D. C., et al., *Biochim. Biophys. Acta* 1281:139–149 (1996)).

Another proposed polynucleotide-liposome composition includes a polynucleotide entrapped in the aqueous interior of neutral liposomes formed from neutral vesicle-forming lipids. These liposomes are typically prepared by either hydrating a dried lipid film with a highly concentrated solution of the polynucleotide (Juliano, R. L., and Akhtar, S., *Antisense Res. Dev.* 2:165–176 (1992)) or by the reverse evaporation method (REV) (Ropert, C., et al., *Pharm. Res.* 10(10):1427–1433 (1993); Szoka, F. C., and Papahadjopoulos, D., *Proc. Natl. Acad. Sci. USA* 75(9):4194–4198 (1978)). A problem with polynucleotide-liposome compositions prepared by these methods is a low trapping efficiency of the polynucleotide, in particular for small unilamellar vesicles (<100 nm), where trapping efficiencies on the order of 2–4% have been reported (Zelphati, O., et al., *Antiviral Res.* 25:13–25 (1994)). Because polynucleotides are expensive, such low trapping efficiencies are unacceptable. The problem is compounded in that recovery of unentrapped polynucleotide can be costly and/or time consuming.

SUMMARY OF THE INVENTION

Accordingly, it is an object of the invention to provide a composition for in vivo administration of a polynucleotide, where the polynucleotide is entrapped in the central core of a liposome.

It is another object of the invention to provide a method for preparing such a composition which achieves a high trapping efficiency of the polynucleotide in the liposome.

It is another object of the invention to provide a liposome composition that is stable in vivo, as evidenced by absence of aggregation of the liposomes in in vitro testing.

It is another object of the invention to provide a liposome composition having a long blood circulation lifetime and an entrapped polynucleotide.

In one aspect, the invention includes a liposome composition for in vivo administration of a polynucleotide. The composition includes a suspension of liposomes composed predominantly of liposomes having a bilayer membrane formed of a cationic vesicle-forming lipid and a neutral vesicle-forming lipid. The liposomes have a central core with an inner surface, and entrapped in the core and localized predominantly on the inner surface is the polynucleotide.

In one embodiment, the polynucleotide is DNA, RNA, or a fragment or an analog thereof. In another embodiment, the polynucleotide is an antisense oligonucleotide.

The cationic lipid is, for example, 1,2-dioleoyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3β[N-(N',N'-dimethylaminoethane) carbamoly] cholesterol (DC-Chol); or dimethyldioctadecylammonium (DDAB).

The neutral vesicle-forming lipid is, in one embodiment, a phospholipid. In another embodiment, the neutral lipid is derivatized with a hydrophilic polymer, such as polyethylene glycol.

Typically, the liposomes have sizes of less than 300 nm, preferably between about 50–300 nm.

In another embodiment, the liposomes further include a ligand for targeting the liposomes to a selected site in the body, such as a particular tissue region or cell.

In another aspect, the invention includes a method of entrapping a polynucleotide in liposomes. The method includes forming polynucleotide-cationic lipid particles in a lipid solvent suitable for solubilization of the cationic lipid. Neutral vesicle-forming lipids are added to the lipid solvent containing the particles, and the lipid solvent is evaporated to form liposomes having the polynucleotide entrapped therein.

The polynucleotide-cationic particles, in one embodiment, are formed by dissolving the polynucleotide in a non-ionic solvent which is immiscible with the lipid solvent. The dissolved polynucleotide is contacted with a charge-neutralizing amount of cationic lipid solubilized in the lipid solvent in the presence of a third solvent effective to form a single phase solvent system, e.g., a monophase. Additional non-ionic solvent or lipid solvent is added to the single phase system under conditions effective to form a two-phase system, and the non-ionic solvent phase is removed.

In one embodiment, the polynucleotide is dissolved in water and is contacted with cationic lipids solubilized in chloroform in the presence of methanol.

Evaporation of the lipid solvent, in one embodiment, includes hydrating with an aqueous medium.

In another aspect, the invention includes a method of administering a polynucleotide to a subject by administering to the subject a suspension of liposomes as described above.

These and other objects and features of the invention will be more fully appreciated when the following detailed description of the invention is read in conjunction with the accompanying drawings.

DETAILED DESCRIPTION OF THE INVENTION

. Liposome Preparation and In Vitro Characterization

The liposome composition of the invention is composed of liposomes, typically in suspension form, having a poly-nucleotide entrapped in the central core. As will be described below and will be apparent from the method of preparation, the liposomes in the suspension have a lipid bilayer composed of a cationic vesicle-forming lipid and a neutral vesicle-forming lipid. The entrapped polynucleotide is associated with the cationic vesicle-forming lipid and is localized predominantly on the inner surface of the central core compartment of each liposome.

Figure 1:
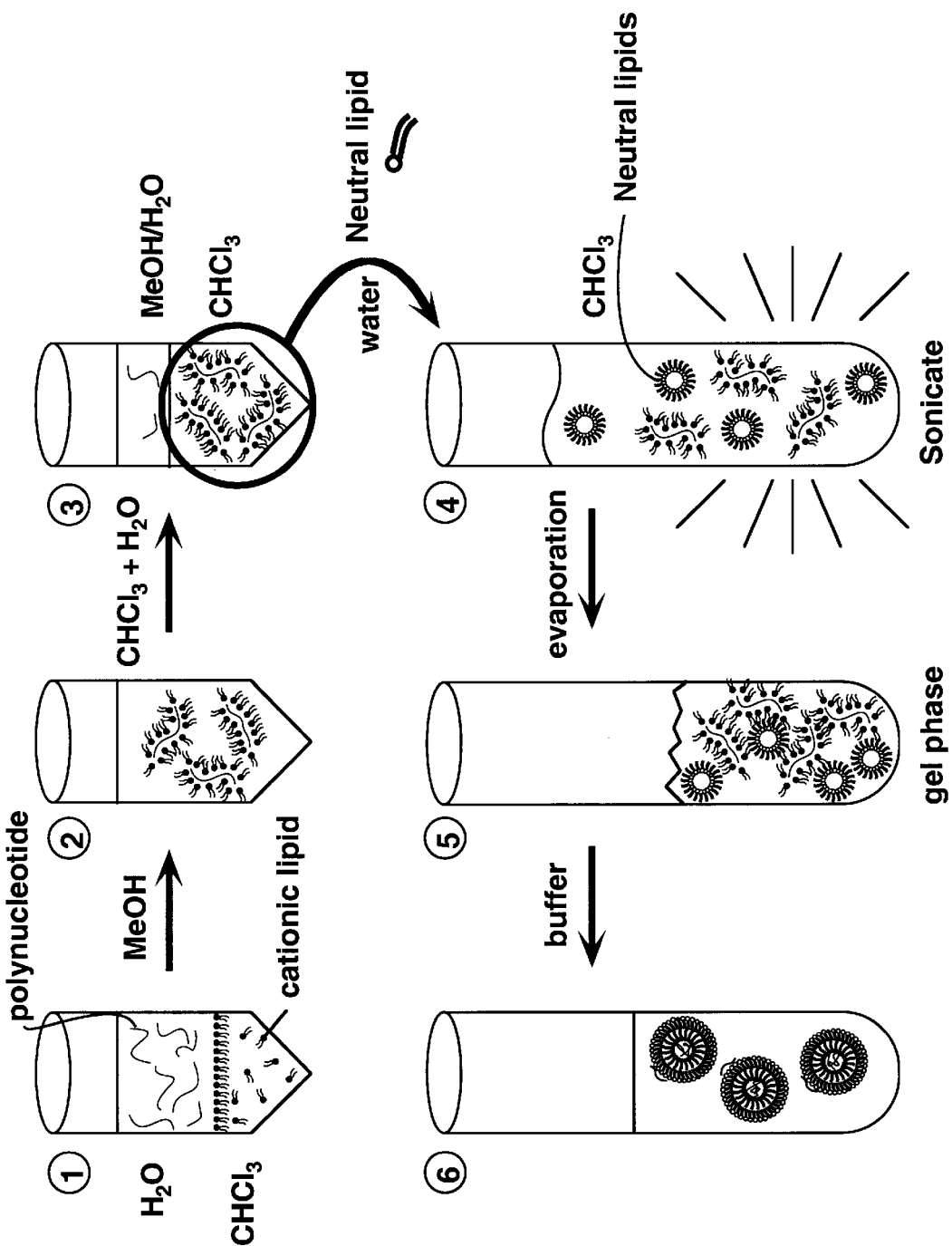
FIG. 1 is a schematic illustration showing formation of liposomes in accordance with the invention by an extraction and evaporation procedure.

With reference to FIG. 1, a method for preparing the liposome composition of the invention is illustrated. In the method, a polynucleotide-cationic lipid particle is formed by extracting the polynucleotide through a Bligh and Dyer monophase (Bligh, E. G., and Dyer, W. J., *Can. J. Biochem. Physiol.* 37(8):911–917 (1959)). The polynucleotide is dissolved in a first solvent, typically a non-ionic solvent, at a selected concentration. Exemplary first solvents include deionized water and non-aqueous, hydrophilic solvents. The non-ionic solvent may contain a non-electrolyte solute, such as sucrose, glucose, dextran and the like.

A cationic lipid of choice is solubilized in a suitable second solvent, also referred to herein as a lipid solvent, which is immiscible with the first solvent in which the polynucleotide is dissolved. For example, the lipid solvent can be chloroform, tetrachloromethane, trichloroethylene, trichloroethane, benzene, hexane, pentane, toluene and the like.

The dissolved polynucleotide and cationic lipid are brought in contact in the presence of a third solvent effective to form a monophase, e.g., a single phase solvent system (tube #2 in FIG. 1). Such a third solvent can be an alcohol, such as methanol or ethanol, a ketone, such as acetone, or an ether. Solvents suitable for the third solvent, e.g., a solvent effective to form a monophase in the presence of the first solvent and the second lipid solvent, can be determined by solubility experiments readily performed by those of skill in the art.

With continuing reference to FIG. 1, the monophase is incubated and an amount of the first solvent and/or the lipid solvent is added to separate the monophase into a two-phase solvent system (tube #3 in FIG. 1). The less dense solvent is removed from the system by aspirating or decanting. It will be appreciated that at this point, each phase can be analyzed for polynucleotide content to determine the extraction efficiency, which is indicative of the liposome loading efficiency.

At this point in the method of preparation, a particle referred to herein as a polynucleotide-cationic lipid particle is formed. It will be appreciated that the amounts of polynucleotide and cationic lipid can be selected to achieve a charge-neutralized polynucleotide-cationic lipid particle or a charged particle. As will be discussed below, studies in support of the invention show that the uptake of the liposomes by the reticuloendothelial system are affected by the degree of charge interaction between the cationic lipid and the anionic polynucleotide.

As illustrated in tube #4 of FIG. 1, neutral vesicle-forming lipids are added to the organic phase containing the polynucleotide-cationic lipid particles. An amount of non-ionic solvent is added and the mixture is mixed briefly by vortexing and/or sonication. The organic phase is then evaporated under rotary evaporation to form a gel phase (tube #5 in FIG. 1). After sufficient evaporation of the organic phase, the system reverts into the aqueous phase to form liposomes having a bilayer lipid membrane of the neutral vesicle-forming lipids and the cationic lipids with the polynucleotide entrapped in the central core of the liposomes. The neutral vesicle-forming lipids are predominantly in the outer lipid bilayers, with the cationic lipids in the inner lipid bilayers closest to the central core of the liposomes. The polynucleotide, which is associated with the cationic lipids, is predominantly on the inner surface regions of the central core compartment. It will be appreciated that a minor fraction of vesicles of another composition and arrangement of lipids may be present in the suspension, but the population of vesicles is predominantly liposomes as described above.

In studies performed in support of the invention, a polynucleotide-cationic lipid complex was prepared using antisense oligonucleotides having 18 and 21 residues. Example 1 describes preparation of polynucleotide-cationic lipid particles composed of a 18-residue oligonucleotide and the cationic lipid dioleoyl trimethylammonium propane (DOTAP). In this study, the amount of DOTAP required to balance the charge of the 18-mer oligonucleotide was determined. As described in Example 1, a fixed amount of the oligonucleotide, including a trace of $^{125}$I-oligonucleotide, was dissolved in a non-ionic solvent (deionized water) and mixed with varying amounts of DOTAP dissolved in chloroform. An amount of methanol sufficient to form a monophase was added. After incubation, the monophase mixture was disrupted to form a biphase solvent system by addition of water and chloroform.

Figure 2:
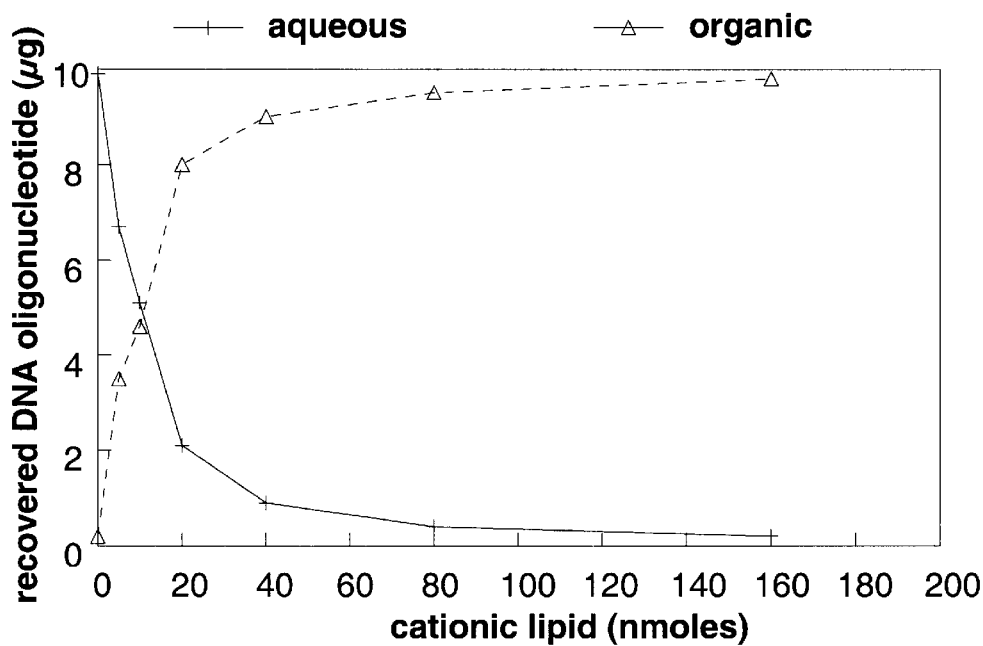
FIG. 2 is a plot showing the amount of oligonucleotide recovered, in µg, upon extraction into an organic phase containing varying amounts of the cationic lipid dioleoyl trimethylammonium propane (DOTAP), where the plus symbols/solid line indicates the amount of oligonucleotide in the aqueous phase and the open triangles/dashed line shows the amount of oligonucleotide in the organic phase.

The aqueous phase and the organic phase were analyzed for labelled oligonucleotide and the results are shown in FIG. 2, which shows the amount of $^{125}$I-oligonucleotide in the organic phase (open triangles/dashed line) and in the aqueous phase (plus symbols/solid line) as a function of nmoles of cationic lipid, DOTAP. As seen, at low cationic lipid concentrations, most of the oligonucleotide remained in the non-ionic, aqueous phase. As the concentration of cationic lipid increased, more oligonucleotide is recovered in the lipid organic phase and at about 80 nmoles of DOTAP, essentially all of the oligonucleotide is extracted into the organic, lipid solvent. At this point, the molar ratio of oligonucleotide to cationic lipid is about 1:50 and the +/− charge ratio is 3:1.

Other studies performed in support of the invention were performed to illustrate the effect of the solvents on the extraction procedure for formation of the polynucleotide-cationic lipid particles. In these studies the procedure described in Example 1 was performed using an ionic aqueous solvent, Hepes buffer (25 mM Hepes, 140 mM NaCl, pH 7.4). In the presence of the ionic buffer, the oligonucleotide was not extracted into the organic phase, presumably due to a charge-shielding interaction. In other studies, a 10% aqueous sucrose solution was used for the extraction with results similar to those described in FIG. 2.

It will be appreciated that the procedure described above for a 18-residue oligodeoxynucleotide and the cationic lipid DOTAP can be used for any selected polynucleotide and cationic lipid combination. Exemplary polynucleotides include DNA, RNA and fragments and analogs thereof; oligonucleotides of up to about 100 nucleotide residues, including oligonucleotides with nuclease resistant chemical linkages, such as phosphorothioate and methylphosphonate.

It will be appreciated that in embodiments where the polynucleotide is, for example, DNA, the polynucleotide can be condensed using a polycationic condensing agent in addition to or instead of the cationic lipid. For example, spermine, spermidine, histones, poly-lysine and protamine sulfate are polycationic agents suitable for condensing a large polynucleotide to facilitate its entrapment in the liposomes of the invention.

Cationic lipid as used herein refers to a vesicle-forming lipid having a net positive charge. The cationic lipid can be a monocation or a polycation. As defined herein, "vesicle-forming lipid" is intended to include any amphipathic lipid having hydrophobic and polar head group moieties, and which by itself can form spontaneously into bilayer vesicles in water, as exemplified by phospholipids. Typically, such vesicle-forming lipids are diacyl-chain lipids, such as a phospholipid, whose acyl chains are typically between about 14–22 carbon atoms in length, and have varying degrees of unsaturation.

Exemplary cationic vesicle-forming lipids include phospholipids, such as phosphatidylethanolamine, whose polar head groups are derivatized with a positive moiety, e.g., lysine, as illustrated, for example, for the lipid DOPE derivatized with L-lysine (LYS-DOPE) (Guo, L., et al., *Journal of Liposome Research* 3(1):51–70 (1993)). Also included in this class are the glycolipids having a cationic polar head-group. Another cationic vesicle-forming lipid which may be employed is cholesterol amine and related cationic sterols.

Other examples include 1,2-dioleoyloxy-3-(trimethylamino) propane (DOTAP); N-[1-(2,3,-ditetradecyloxy)propyl]-N,N-dimethyl-N-hydroxyethylammonium bromide (DMRI E); N-[1-(2,3,-dioleyloxy)propyl]-N,N-dimethyl-N-hydroxyethylammoniumbromide(DORIE); N-[1-(2,3-dioleyloxy) propyl]-N,N,N-trimethylammonium chloride (DOTMA); 3β[N-(N',N'-dimethylaminoethane) carbamoly] cholesterol (DC-Chol); and dimethyldioctadecylammonium (DDAB).

The above-described lipids can be obtained commercially, or prepared according to published methods.

A variety of neutral lipids are suitable for use in the present invention. Neutral vesicle-forming lipids, meaning vesicle forming lipids which have no net charge, include phospholipids, such as phosphatidylcholine, phosphatidyl ethanolamine, phosphatidylinositol, and sphingomyelin. Negatively charged lipids are also contemplated for use alone or in combination with a neutral lipid. Exemplary negative vesicle-forming lipids include phosphatidylserine, phosphatidylglycerol and phosphatidic acid. It will be appreciated that other lipids, such as cholesterol and other uncharged sterols, can be added to the neutral or negatively charged vesicle-forming lipid and that various combinations are suitable for use.

Example 2 describes formation of liposomes following formation of oligonucleotide-cationic lipid particles by the extraction procedure discussed above in Example 1. Cationic lipid-oligonucleotide particles were prepared using the cationic lipid DOTAP and a 21-residue oligonucleotide by dissolving 50 μg of the oligonucleotide in a non-ionic aqueous phase and 0.5 μmoles DOTAP in a lipid organic phase. The oligonucleotide was extracted from the aqueous phase to form oligonucleotide-cationic lipid particles.

Added to the oligonucleotide-cationic lipid particles was a selected amount of phosphatidylcholine (iodine number 40) and cholesterol in a 2:1 ratio (PC:chol). A small amount of deionized water was added, the mixture was sonicated briefly to emulsify the phases and the organic phase was evaporated. Liposomes formed once the system reverted into the aqueous phase. As described above, the entrapped oligonucleotides are associated predominantly with the inner surface of the central core region due to the charge interaction between the cationic lipid and the oligonucleotides. The neutral lipids coat the particles, to form a liposomal bilayer composed of both the cationic lipids, which are primarily disposed in the inner bilayer region of the liposomes, and the neutral lipids, which are disposed in the outer bilayer regions of the liposomes and form a coating around the cationic-polynucleotide particles.

Liposomes having entrapped oligonucleotides, prepared as described in Example 2, were characterized by dynamic light scattering and on a metrizamide density gradient column to determine encapsulation efficiency. As described in Example 3, the suspension of liposomes was placed on a metrizamide gradient column to separate the liposomes containing entrapped oligonucleotide from unentrapped oligonucleotide. Unentrapped oligonucleotide equilibrates in a lower, more dense column fraction, e.g., the 20% metrizamide fraction whereas the liposomes equilibrate in a less dense fraction. After the liposomes sample was placed on the column, the gradient column was centrifuged. After centrifugation, the liposome fraction of the sample had equilibrated at the 10% metrizamide/water interface, with a faint band of lipid visible at the 20%/10% metrizamide interface. The lipid was collected from the 10% metrizamide/water interface for counting in a gamma counter and for assaying for phosphate content.

TABLE 1

| Phosphatidylcholine ($\mu$moles) | Size* (nm) | Encapsulation Efficiency* (%) | Polynucleotide/ phospholipid Ratio* (nmol/$\mu$mol) |
| --- | --- | --- | --- |
| 0.5 | 360 ± 60 | 72 ± 10 | 7.9 ± 2.1 |
| 1.0 | 530 ± 170 | 74 ± 4 | 5.4 ± 0.4 |
| 2.0 | 510 ± 200 | 73 ± 10 | 3.4 ± 0.5 |

*value ± standard deviation for n = 3.

Table 1 shows the results for three liposomal compositions containing different amounts of phosphatidylcholine. The encapsulation efficiency, taken as the counts in the liposome-associated oligonucleotide fraction over the total number of counts measured in the column, is around 73%, a significant improvement over that achieved by passive entrapment.

Also shown in Table 1 are the liposomal particle size measurements, determined by dynamic light scattering. The liposomes were between 360–530 nm in diameter, somewhat larger than preferred for in vivo administration, where liposomes having sizes of less than about 300 nm are preferred. Sizing of the liposomes down to the preferred size was demonstrated by extruding through 100 nm or stacked 200 nm filters. These extrusions demonstrated that the liposomes can be successfully down-sized while retaining the entrapped oligonucleotide. The extrusion experiments also demonstrated that the neutral lipid stabilizes the liposomes, as evidenced by liposomes having about 2 $\mu$moles neutral lipid were more stable during the extrusion.

In one embodiment of the invention, the liposomes include a surface coating of hydrophilic polymer chains, effective to extend the blood circulation time of the liposomes. Suitable hydrophilic polymers include polyethylene glycol (PEG), polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethyl-cellulose. A preferred hydrophilic polymer chain is polyethyleneglycol (PEG), preferably as a PEG chain having a molecular weight between 500–10,000 daltons, more preferably between 1,000–5,000 daltons.

The coating is preferably prepared by including in the neutral vesicle-forming lipids forming the liposomes, between 1–20 mole percent of a vesicle-forming lipid, preferably a phospholipid or other diacyl-chain lipid, derivatized at its head group with the polymer chain. Exemplary methods of preparing such lipids, and forming polymer coated liposomes therewith, have been described in co-owned U.S. Pat. Nos. 5,013,556, 5,631,018 and 5,395,619, which are incorporated herein by reference. The polymer may be stably coupled to the lipid, or coupled through an unstable linkage which allows the coated particles to shed their coating as they circulate in the bloodstream.

Liposomes having such a surface coating and including an entrapped polynucleotide were prepared using methoxy polyethylene glycol (mPEG) derivatized to distearoyl phosphatidylethanolamine (DSPE). As described in Example 3, oligonucleotide-cationic lipid particles were formed and liposomes were prepared by adding to the particles neutral lipids composed of a 2:1:0.1 molar ratio of phosphatidylcholine, cholesterol, and mPEG$_{2000}$ covalently attached to the polar head group of DSPE, mPEG-DSPE. The resulting liposome suspension was extruded through polycarbonate filters to diameters below 200 nm.

Figure 3:
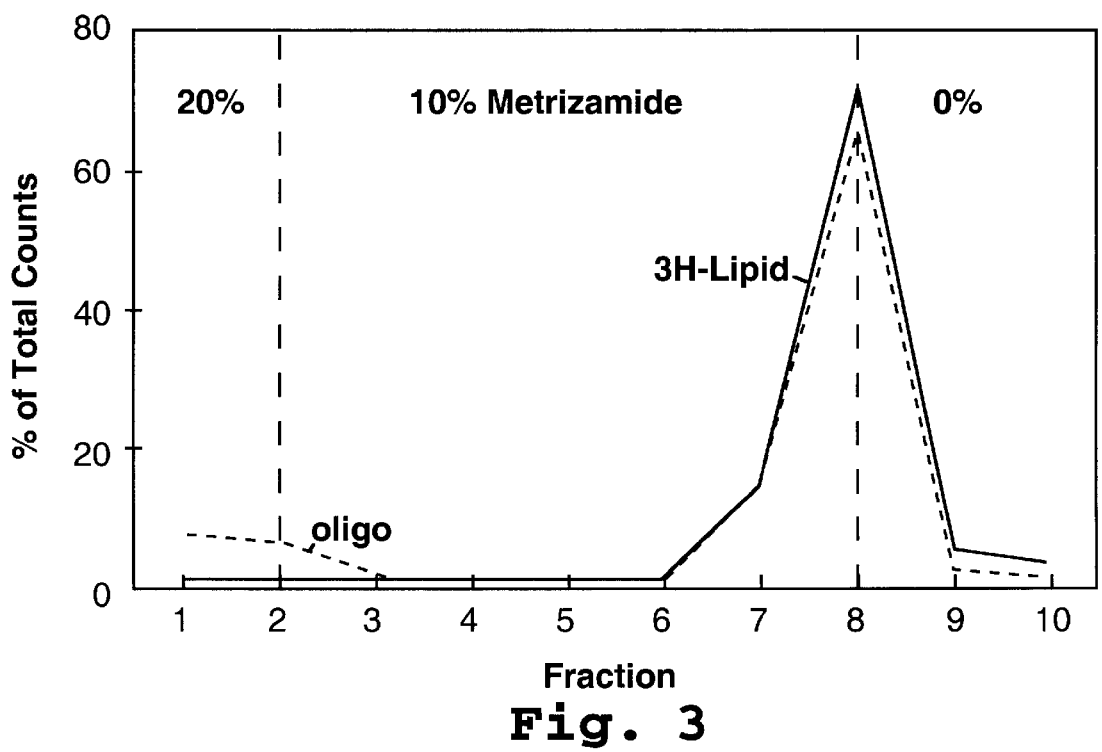
FIG. 3 is a density gradient profile for cationic labelled lipid (solid line) and polynucleotide (dashed line), shown as the percentage of total counts against fraction number.

The encapsulation efficiency of the oligonucleotide into the PEG-coated liposomes was determined by separating the liposomes from unentrapped oligonucleotide on a metrizamide gradient, as described in Example 3. The separation profile of the liposome suspension is shown in FIG. 3, where the percentage of total counts on the gradient column is shown as a function of fraction number. As seen in the figure, nearly all of the lipid migrated to the 10% metrizamide/deionized H$_2$O interface, and except for a very small amount in the first two fractions, all of the oligonucleotide migrated with the lipid. Table 2 summarizes the results from two separate experiments.

TABLE 2

| Neutral Lipid Added ($\mu$moles) | Size (nm) | Encapsulation Efficiency (%) | Ratio* oligonucleotide/ phospholipid (nmol/$\mu$mol) |
| --- | --- | --- | --- |
| 3 | 174 | 86 | 2.1 |
| 3 | 176 | 91 | 2.2 |

*Calculated based on the starting oligonucleotide:phospholipid ratio, and then correcting for % of oligonucleotide not associated with lipid.

The data in Table 2 shows that for a liposome having a size of about 175 nm, a size suitable for in vivo administration, the encapsulation efficiency was around 90%, a considerable improvement over the 10% efficiency reported in the literature for liposomes prepared by other procedures (Ropert, et al., 1993). The oligonucleotide to phospholipid ratio is around 2 nmol/$\mu$mol.

In another embodiment of the invention, the liposomes include a ligand or affinity moiety effective to bind specifically to a desired tissue region or target cell. Such moieties can be attached to the surface of the liposome or to the distal ends of hydrophilic polymer chains. Exemplary moieties include antibodies, ligands for specific binding to target cell surface receptors and the like, as described, for example, in co-owned PCT application No. WO US94/03103.

A. Liposome Stability

The stability of the liposomes in 25% fetal bovine serum was determined by preparing liposomes having an entrapped oligonucleotide and measuring liposome size as a function of time after placing in the serum.

In this study, the liposomes were prepared in accordance with the method of the invention and were composed of a 21-residue oligodeoxynucleotide, the cationic lipid DOTAP, and neutral lipids consisting of 5 mol % MPEG-DSPE, 2 μmoles phosphatidylcholine and 1.25 μmoles cholesterol (PC:Chol:mPEG-DSPE molar ratio of 2:1:0.1).

Two liposome suspensions were prepared using these components. In the first liposome suspension, deionized water was used for formation of the cationic-lipid-oligonucleotide particles and as the hydration medium for liposome formation during solvent evaporation. In the second suspension, a 5% sucrose aqueous solution was used rather than water.

The size of the liposomes after extrusion was 174 nm, for the liposomes prepared in deionized water, and 172 nm, for the liposomes prepared in 5% sucrose, as seen in Table 3.

A sample of each liposome suspension was placed in buffer (25 mM Hepes, 140 mM NaCl, pH 7.4) and the particle size was measured again, as seen in Table 3. The liposomes in both suspensions were reduced in size, to around 156 nm and 157 nm for the water-based and the 5% sucrose-based suspensions, respectively.

A sample of each liposome suspension was placed in a solution of 25% fetal bovine serum in buffer and the liposome particle size was measured immediately and at 24 hour intervals after storing at 37° C. As seen in Table 3, the liposomes in each suspension experience some change in particle size as the particles equilibrate to balance the inner and outer osmotic strengths. Importantly, no aggregation of the liposomes was observed, indicating that the liposomes should be stable after in vivo administration.

197±2 nm (polydispersity 0.032±0.012) while the cationic liposomes of the invention had an average diameter of 188±1 nm (polydispersity 0.138±0.018).

Both liposome compositions were administered to mice according to the procedure of Example 6. Free oligonucleotide was also administered to a group of test animals. The compositions were intravenously administered in a single bolus injection via the tail vein at a lipid (phosphatidylcholine) dose of 0.5 μmoles. At specific time points three mice from each test group were sacrificed and the organs and a blood sample were analyzed for presence of oligonucleotide.

Figure 5:
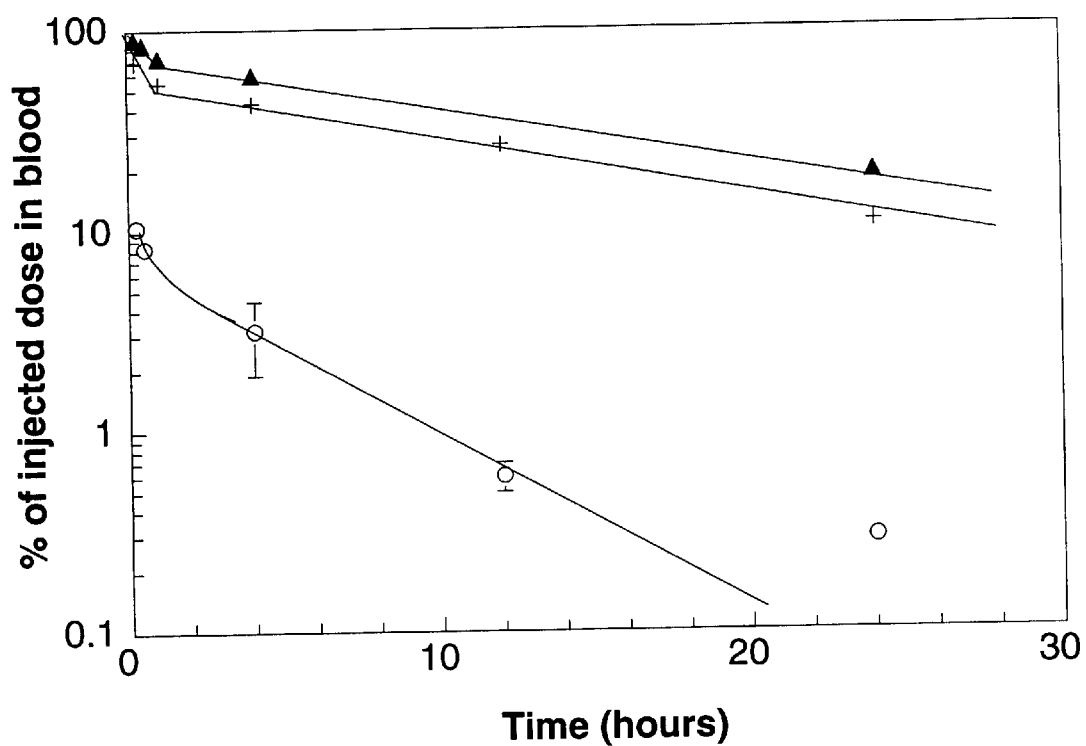
FIG. 5 is a plot showing the percentage of injected dose in the blood as a function of time following intravenous injection into mice of free oligonucleotide (open circles), oligonucleotide entrapped in neutral liposomes (closed triangles) and in cationic liposomes prepared in accordance with the invention (plus symbols)

FIG. 5 shows the blood circulation lifetime of the free oligonucleotide (open circles) and the liposome entrapped oligonucleotide, where the liposomes of the invention are represented by the plus symbols and the comparative, neutral liposomes by the closed triangles. As seen in the figure, free $^{125}$I-labelled oligonucleotide has an initial, rapid distribution phase and approximately 50% of the injected dose has been eliminated from the body 2 hours after administration.

In contrast, $^{125}$I-labelled oligonucleotide encapsulated within liposomes demonstrate a much different pharmacokinetic profile in the blood. Encapsulated within neutral liposomes (closed triangles), the oligonucleotide has a short initial phase of elimination immediately following injection which accounts for about 10% of the injected dose. The remaining 90% of the dose has a much slower rate of elimination, so that at 24 hours following injection, about 20% of the injected dose remains in blood.

$^{125}$I-labelled oligonucleotide entrapped within the cationic liposomes of the invention displayed a similar profile,

TABLE 3

| Tube # | Neutral Lipid (μmoles) | Aqueous Phase | Size After Extrusion (nm) | Size in Hepes 7.4 (nm) | Size in 25% FBS (nm) | | |
| --- | --- | --- | --- | --- | --- | --- | --- |
| | | | | | 0 hrs. | 24 hrs. | 48 hrs. |
| 1 | 2 | deionized H$_2$O | 174 | 156 | 171 | 160 | 165 |
| 2 | 2 | 5% sucrose | 172 | 157 | 226 | 166 | 198 |

II. In vivo Characterization of the Liposomes

Liposomes were prepared in accordance with the invention to include an 18-mer phosphorothioate oligonucleotide complementary to the MDRI gene. The liposomes used for the in vivo studies included a surface coating of polyethylene glycol (PEG) hydrophilic polymer chains, by including in the neutral liposome composition distearoyl phosphatidylethanolamine derivatized with PEG (mPEG$_{200}$-DSPE), as described in Example 5B. For comparison, neutral liposomes were prepared by a conventional lipid film hydration in the presence of the oligonucleotide (Example 5A).

Figure 4A:
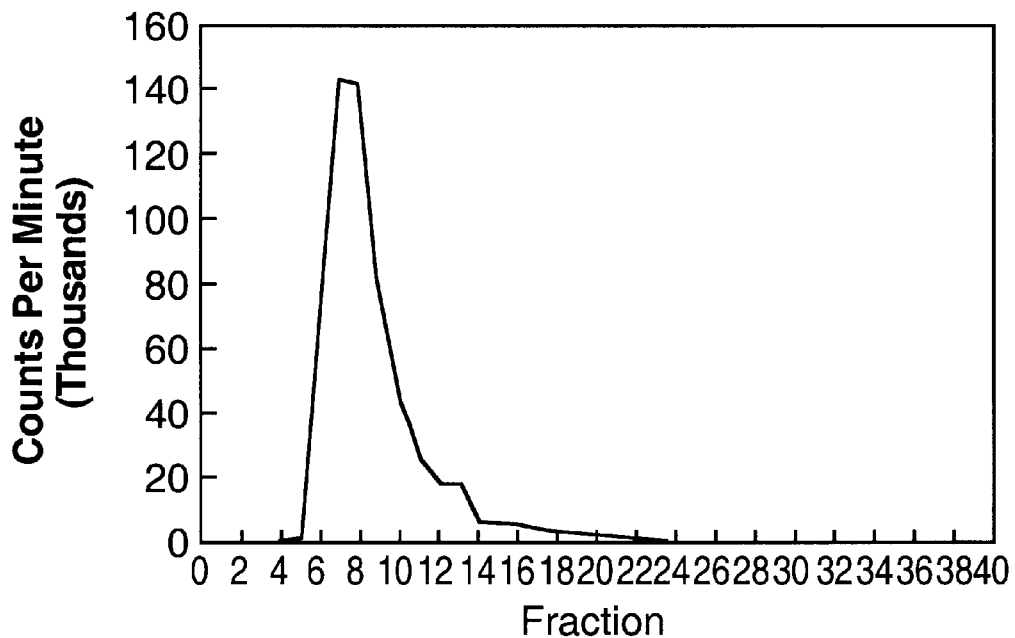
FIGS. 4A–4B are fractionation profiles following separation down a Sepharose column of a liposome composition with an entrapped polynucleotide in accordance with the invention (FIG. 4A) and a comparative liposome composition formed of neutral vesicle-forming lipids (FIG. 4B)
Figure 4B:
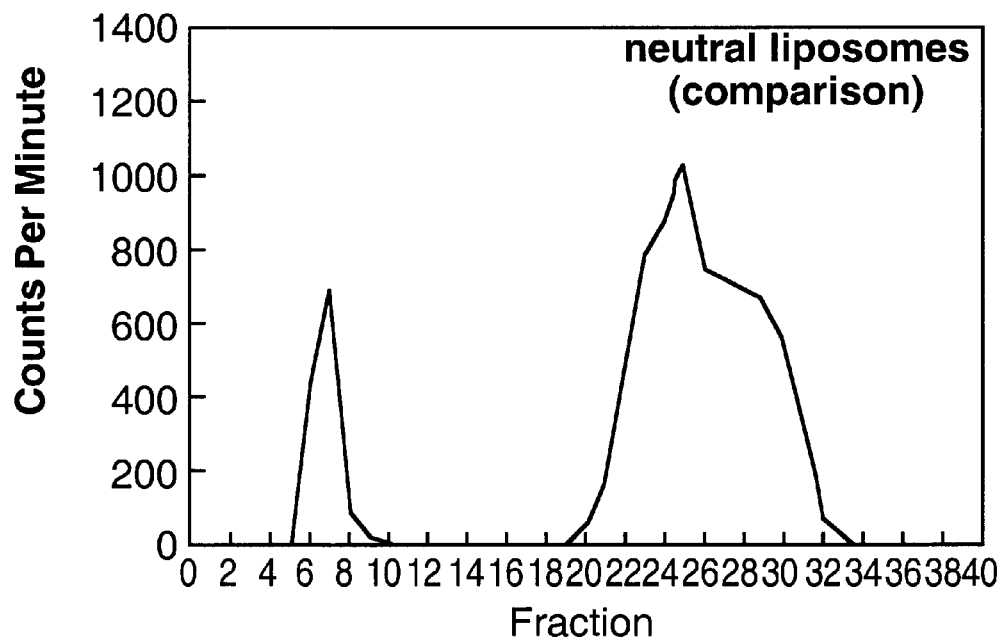

FIGS. 4A–4B are fractionation profiles for the cationic liposomes (FIG. 4A) and the neutral liposomes (FIG. 4B) prepared for the animal studies. The profiles were obtained by sampling the fractions during separation of the free oligonucleotide from the lipid associated oligonucleotide by filtration down a Sepharose CL-4B column (Example 5B). As seen in FIG. 4A, virtually 100% of the oligonucleotide was associated with the lipid fraction, as evidenced by the single elution peak over fractions 5–12. In contrast, as seen in FIG. 4B, only 20% of the oligonucleotide was associated with the neutral liposomes.

The liposomes were sized by dynamic light scattering and the conventional liposomes had an average diameter of however, the initial phase of elimination accounted for approximately 30% of the injected dose. Twenty-four hours following injection, over 10% of the injected dose remained in the blood.

Table 4 gives the pharmacokinetic parameters calculated for each treatment. The residence time corresponds to the time required for 66% of the administered dose to be eliminated from the blood, and the liposome formulations result in a significant improvement in residence time. The area under the curve (AUC) values for the liposome formulations are also significantly higher than for the free oligonucleotide. The AUC for oligonucleotide entrapped within the liposomes of the invention is larger than for neutral liposomes because of the larger dose administered (52.4 μg versus 6.5 μg). As discussed above, the dose administered was based on the amount of lipid rather than amount of oligonucleotide, since the lipid dose can have a significant effect on liposomal pharmacokinetics (Allen, T. M. et al., Biochim. Biophys. Acta 1068:133–141 (1991)) when the entrapped agent has a slow rate of leakage from the liposomes. The amount of oligonucleotide associated with the cationic liposomes is significantly greater than for neutral liposomes, as demonstrated by the entrapment efficiency (FIGS. 4A, 4B) and therefore the amount of oligonucleotide injected per μmole phospholipid is much greater for the cationic liposomes, leading to a larger AUC. When doses are normalized to 30 μg oligonucleotide/mouse (assuming linear pharmacokinetics), the AUC for neutral liposomes (199.9) is greater than for cationic liposomes (128.1) or free oligonucleotide (10.4). It will be appreciated that the improved loading efficiency of the oligonucleotide in the cationic liposomes of the invention permit administration of a smaller lipid dose to achieve a given dose of oligonucleotide, compared to conventional neutral liposomes.

With continuing reference to Table 4, the rapid clearance of free oligonucleotide from the blood is also reflected in the elimination rate constant (k) which is more than 10-fold greater than for both liposomal treatments. The volume of distribution ($V_D$) for both liposomal treatments is close to the blood volume of the animals used, however, for free oligonucleotide the volume of distribution was about 5-fold higher, indicating that it was widely distributed within the tissues.

The blood circulation half-lives ($T_{1/2}$) for the initial phase of elimination ($T_{1/2}\alpha$) and for the elimination of the remaining dose ($T_{1/2}\beta$) are also shown in Table 4.

TABLE 4

| | Pharmacokinetic parameters calculated for oligonucleotide in different formulation | | | | | |
|---|---|---|---|---|---|---|
| Group | Residence Time (hrs) | AUC (μg · hr/ml) | $V_D$ (ml) | k (hr$^{-1}$) | $T_{1/2}\alpha$ (hrs) | $T_{1/2}\beta$ (hrs) |
| Neutral liposomes (6.5 μg) | 17.6 | 43.4 | 1.96 | 0.08 | 0.39 | 12.4 |
| cationic liposomes (52.4 μg) | 15.0 | 226.9 | 2.39 | 0.10 | 0.26 | 10.6 |
| Free oligonucleotide (300 μg) | 4.7 | 5.7 | 13.77 | 0.38 | 0.26 | 3.5 |

Figure 6A:
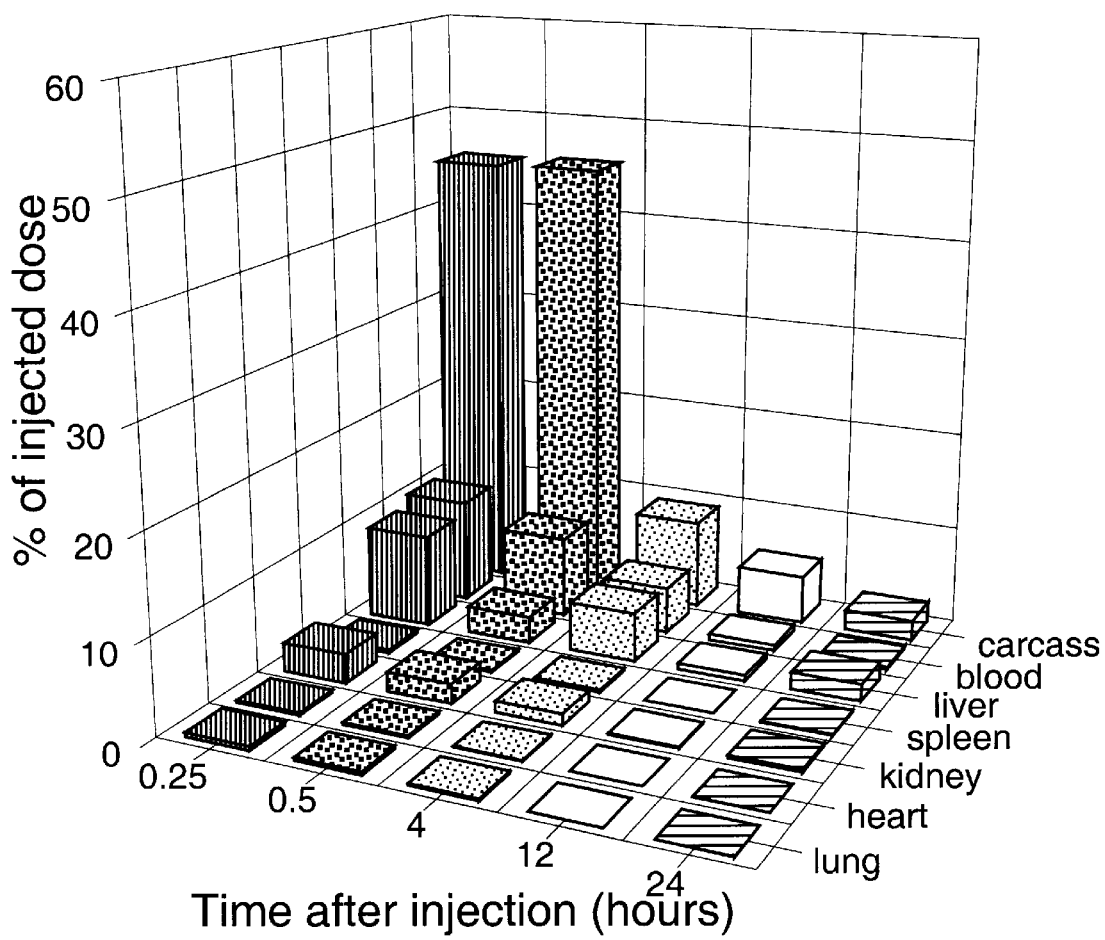
FIGS. 6A–6C are plots showing the biodistribution of an oligonucleotide following intravenous administration to mice in the free form (FIG. 6A), entrapped in neutral liposomes (FIG. 6B) and entrapped in liposomes in accordance with the invention (FIG. 6C)
Figure 6B:
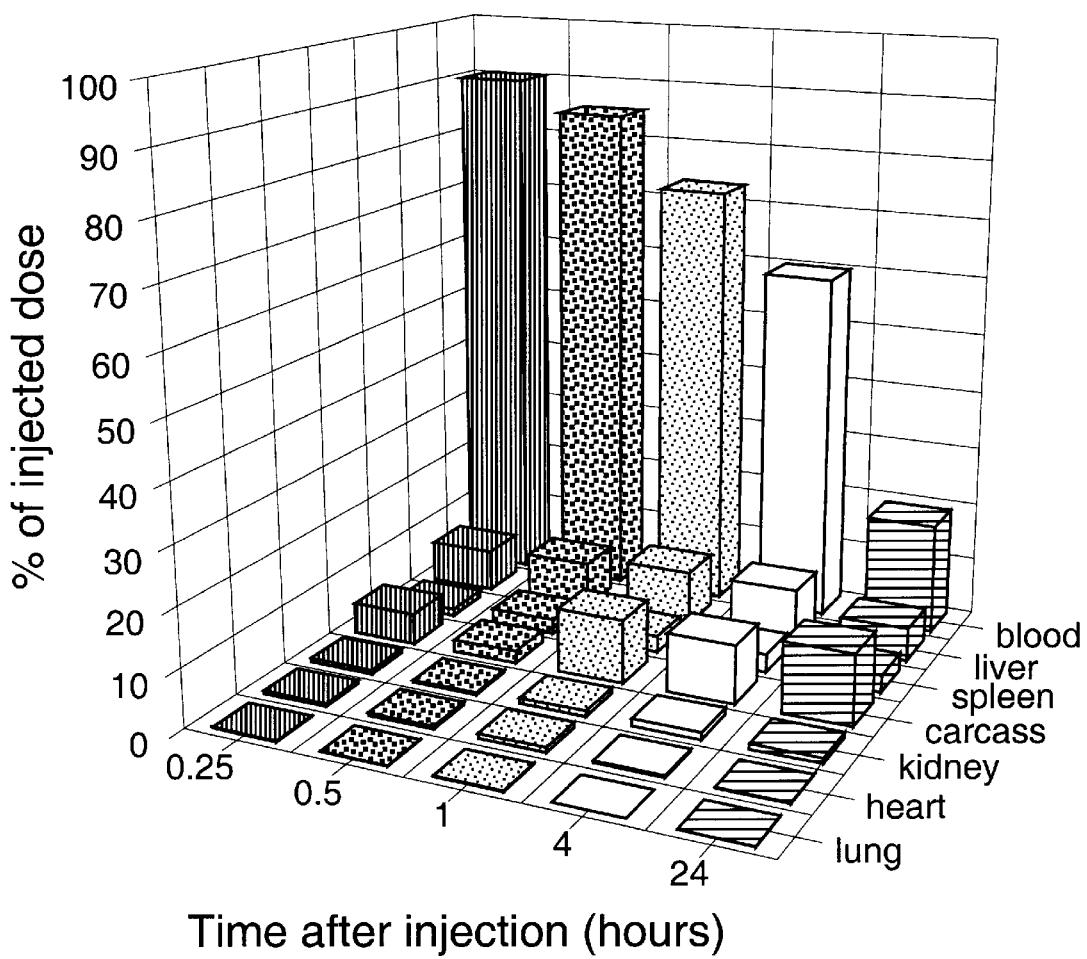
Figure 6C:
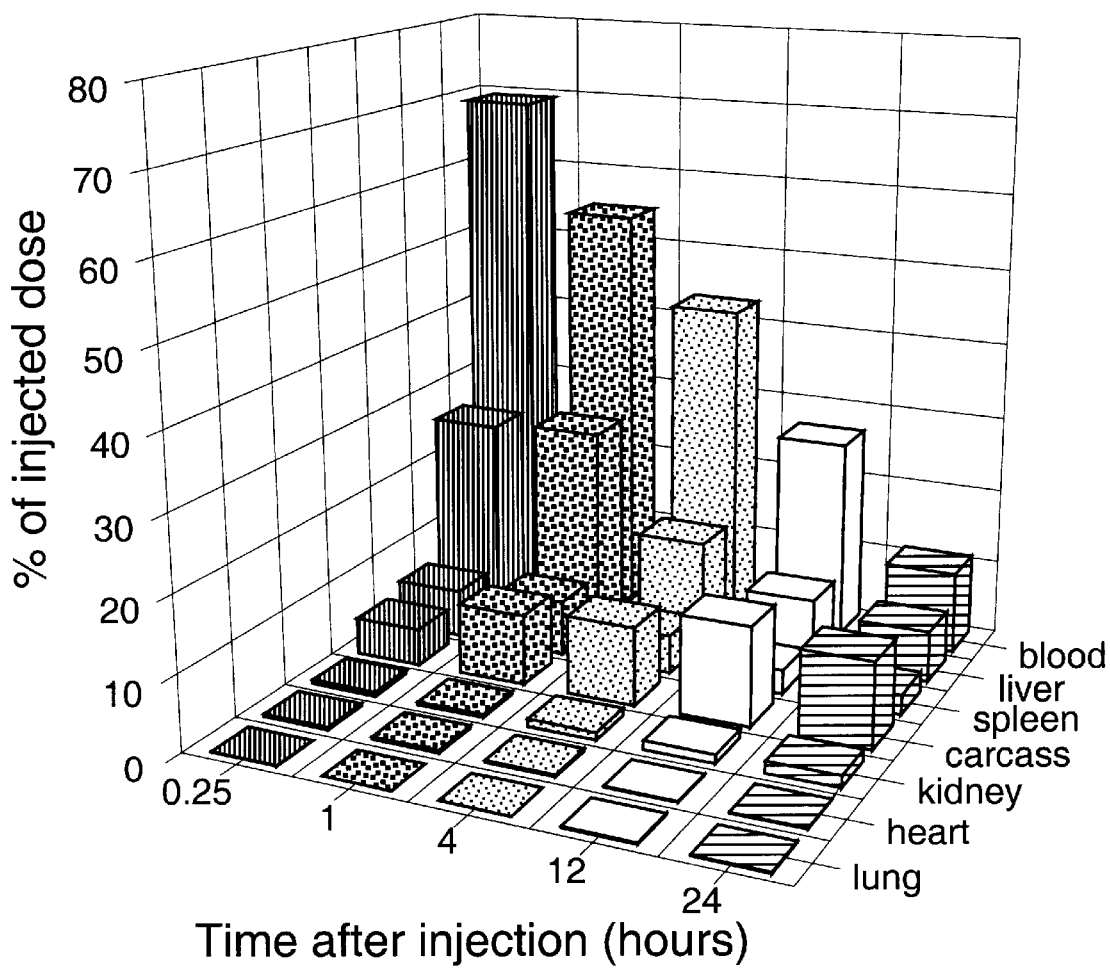

FIGS. 6A–6C are plots showing the biodistribution of the oligonucleotide in the animals, where FIG. 6A corresponds to the distribution after administration of the oligonucleotide in the free form, FIG. 6B corresponds to the oligonucleotide entrapped in neutral liposomes and FIG. 6C corresponds to the oligonucleotide entrapped in cationic liposomes in accordance with the invention.

FIG. 6A shows that very little free oligonucleotide remains in blood any time point after 15 minutes. The greatest proportion of the dose distributes to the carcass which includes all of the remaining tissues left undissected. The liver and kidney also contained significant amounts of radioactive counts.

FIG. 6B shows that at all time points, the greatest proportion of oligonucleotide exists in the blood when administered in the form of neutral liposomes. Blood levels account for nearly all of the dose, particularly at the earlier time points. There is a relatively constant amount in the liver and spleen at all time points, however, carcass levels appear to increase in later time points and this would be consistent with the distribution and elimination of free oligonucleotide following release from the liposomes, or possible the accumulation of liposomal oligonucleotide within tissues.

FIG. 6C shows that oligonucleotide administered entrapped in cationic liposomes the nucleotide remains primarily in the blood. There is an increase in carcass levels over time, consistent with elimination of free oligonucleotide or with the accumulation of liposomal oligonucleotide in the tissues.

In another study, the effect of the oligonucleotide:cationic lipid ratio on uptake of the liposomes by the reticuloendothelial system was studied. Liposomes were prepared by the method of the invention (Example 5B) with ratios of oligonucleotide:cationic lipid (DOTAP) of 0 (no oligonucleotide in the formulation), 44.4 μg/μmole (+/- ratio of 2.6:1) and 104.8 μg/μmole (+/- ratio 1.1:1), In the formulation where the liposomes contained no oligonucleotide, the liposomes were hydrated in the presence of $^{125}$I-labelled tyraminylinulin, prepared as described in Sommerman (Sommerman E. F., et al., *Biochem. Biophys. Res. Comm.*, 122:319–324 (1984)). The liposome formulation were intravenously injected into mice and the liver and spleen were analyzed 15 minutes after administration for $^{125}$I-labelled tyraminylinulin and $^{125}$I-labelled oligonucleotide.

Figure 7:
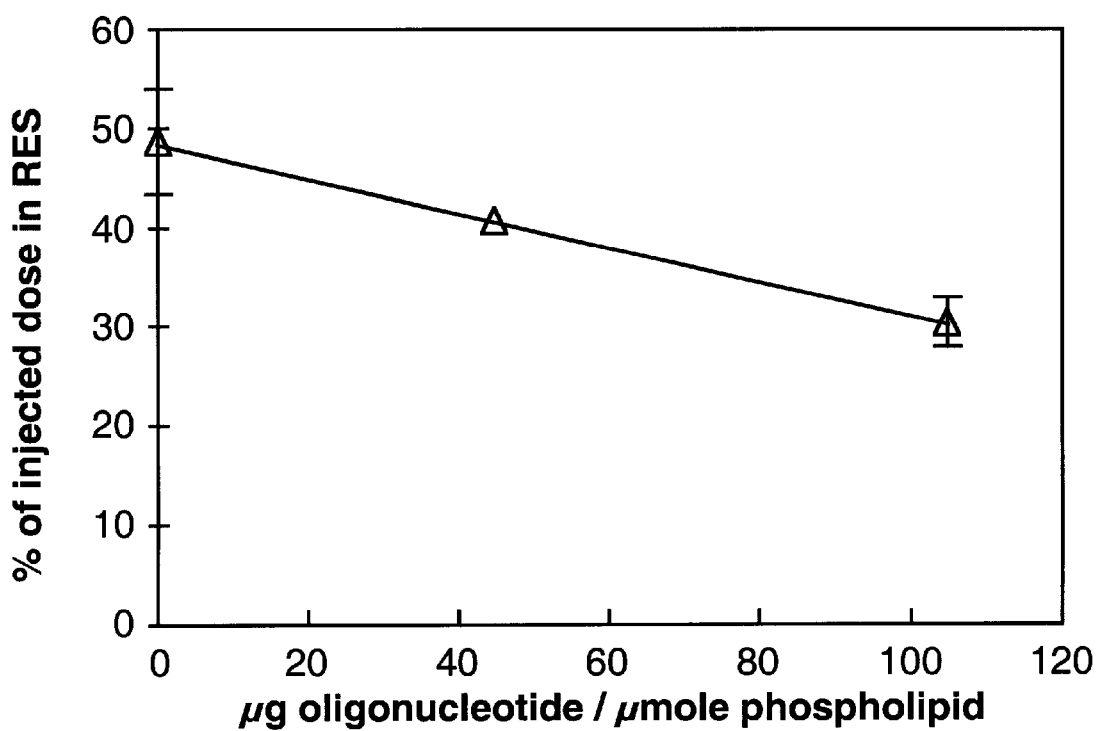
FIG. 7 is a plot showing the reticuloendothelial system uptake of different quantities of an oligonucleotide entrapped in liposomes in accordance with the invention following intravenous administration to mice.

The results are shown in FIG. 7 where the percentage of remaining dose in the reticuloendothelial system is shown as a function of oligonucleo-tide/cationic lipid ratio. For the dose with no oligonucleotide, nearly 50% of the dose distributed to the liver and spleen 15 minutes following injection. When the oligonucleotide/cationic lipid ratio was 44.4 μg/μmole, approximately 40% of the dose distributed to liver and spleen. When the ratio was 104.8 μg/μmole (+/- ratio 1.1:1), approximately 30% of the dose distributed to the liver and spleen 15 minutes following injection. The uptake at 104.8 μg/μmole was significantly different from the uptake at 44.4 μg/μmole and 0 μg/μmole (p<0.05).

III. Method of Administration

In another aspect, the invention includes a method of administering a polynucleotide to a subject. The polynucleotide is entrapped in cationic liposomes as described above and administered to a subject in need of treatment.

The polynucleotide entrapped in the liposomes can be selected from a variety of DNA and RNA based polynucleotides, including fragments and analogues of these. In one embodiment, the polynucleotide is an antisense DNA oligonucleotide composed of sequences complementary to its target, usually a messenger RNA (mRNA) or a mRNA precursor. The mRNA contains genetic information in the functional, or sense, orientation and binding of the antisense oligonucleotide inactivate the intended mRNA and prevents its translation into protein. Such antisense molecules are determined based on biochemical experiments showing that proteins are translated from specific RNAs and that once the sequence of the RNA is known, an antisense molecule that will bind to it through complementary Watson-Crick base pairs can be designed. Such antisense molecules typically contain between 10–30 base pairs, more preferably between 10–25, and most preferably between 15–20.

In one embodiment of the invention, the antisense oligonucleotide is modified for improved resistance to nuclease hydrolysis. Such analogues include phosphorothioate, methylphosphonate, phosphodiester and p-ethoxy oligonucleotides (WO 97/07784, published Mar. 6, 1997).

The composition of the invention is intended for use in a variety of therapies, including, but not limited to, treatment of viral, malignant and inflammatory diseases and conditions, such as, cystic fibrosis, adenosine deaminase deficiency and AIDS. Treatment of cancers by administration of tumor suppressor genes, such as APC, DPC4, NF-1, NF-2, MTS1, RB, p53, WT1, BRCA1, BRCA2, VHL, or administration of oncogenes, such as PDGF, erb-B, erb-B2, RET, ras (including Ki-ras, N-ras), c-myc, N-myc, L-myc, Bcl-1, Bcl-2 and MDM2, are contemplated.

Administration of the following nucleic acids for treatment of the indicated conditions are also contemplated: HLA-B7, tumors, colorectal carcinoma, melanoma; IL-2, cancers, especially breast cancer, lung cancer, and tumors; IL-4, cancer; TNF, cancer; IGF-1 antisense, brain tumors; IFN, neuroblastoma; GM-CSF, renal cell carcinoma; MDR-1, cancer, especially advanced cancer, breast and ovarian cancers; and HSV thymidine kinase, brain tumors, head and neck tumors, mesothelioma, ovarian cancer.

It will be appreciated that the composition of the invention has utility in ex vivo procedures as well.

The liposomes are typically in suspension form, for parenteral administration, preferably intravenous administration. Other routes of administration are suitable, including subcutaneous, intramuscular, interlesional (to tumors), intertracheal by inhalation, topical, internasal, intraocular, via direct injection into organs and intravenous.

From the foregoing, it can be appreciated how various features and objects of the invention are met. The present invention provides a liposome composition having a polynucleotide entrapped in the central core, where, by virtue of the method of preparation, the polynucleotide is associated primarily with the inner surface region of the cationic lipids forming the central core. A coating of neutral lipids surrounds the cationic lipid core, the neutral lipids serving to stabilize the vesicles.

In the embodiment where the liposomes include a surface coating of hydrophilic polymer chains, the liposomes achieved a long blood circulation lifetime, with little uptake by the RES.

Further, the method for preparing the liposomes results in a high encapsulation efficiency of the polynucleotide, where at least about 80% of the polynucleotide is entrapped in the liposomes. In the studies described above, at a 1:1 charge ratio of oligonucleotide:cationic lipid, approximately 95% of the oligonucleotide was extracted from the aqueous phase into the organic phase. Following addition of neutral lipid and liposome formation all of the oligonucleotide remains associated with the lipid (as evidenced by FIG. 4A).

The liposomes can be sized by extrusion, if necessary, to bring the liposome size to a range suitable for in vivo administration, typically, less than about 300 nm, more preferably between 50–300 nm, most preferably between 100–200 nm. The liposomes are stable, as evidenced by no aggregation or appreciable change in size when placed in fetal bovine serum and by low lung and RES uptake in vivo.

IV. EXAMPLES

The following examples illustrate the liposome composition and method of preparation of the present invention. The examples are in no way intended to limit the scope of the invention.

Example 1

Formation of Polynucleotide-Cationic Lipid Particles

A. Preparation of $^{125}$I-labelled oligonucleotide $^{125}$I-labelled oligonucleotide was prepared in the following way: a 1 ml conical reaction vial was coated with approximately 200 μg of Iodogen (Pierce, Rockford, Ill.) and then 500 μg of oligonucleotide was added along with 2,400 pmoles of $^{125}$I (185 Mbq) and 300 μl 0.35 M sodium acetate, pH 4.0 in a total volume of 400 μl (Piatyszek, M. A., *Ana. Biochem.* 172:356–359 (1988)). The mixture was incubated for one hour at 40° C. with frequent agitation. Following incubation, the mixture was removed from the reaction vial and free $^{125}$I was removed by separation on a Sephadex G-25 column. In order to remove residual free $^{251}$I, the sample was precipitated in 0.3 M sodium acetate and 2.5 volumes of 95% ethanol. Free iodine was discarded in the supernatant while labelled oligonucleotide was rehydrated from the pellet and de-salted on a Sephadex G-25 (Pharmacia, Sweden) column equilibrated in double distilled H$_2$O. This resulted in less than 5% free $^{125}$I as determined by thin layer chromatography on PEI-cellulose (J.T. Baker, Inc., Phillipsburg, N.J.).

B. Extraction Procedure to Prepare Particles

Seven vials containing 10 μg of an 18-residue oligonucleotide with a trace of $^{125}$I-oligonucleotide in 0.25 mL distilled deionized water were prepared.

The cationic lipid 1,2-dioleoyl-3-trimethylammonium-propane (DOTAP) (Avanti Polar Lipids, Alabaster, Ala.) was dissolved in chloroform at concentrations ranging from about 1.8 to 1880 nmoles/ml.

0.25 mL of each chloroform-cationic lipid solution and 0.51 mL methanol were added to each vial of oligonucleotide and each vial was vortexed to form a monophase.

After a 30 minute incubation at room temperature, 0.25 mL of distilled, deionized H$_2$O and 0.25 mL of CHCl$_3$ were added to each vial to disrupt the monophase, forming a biphasic system in each vial. The vials were mixed and then centrifuged for 7 minutes at 800×g. The aqueous-methanol layer was aspirated from each vial and saved in a separate tube, and then the amount of oligonucleotide in both phases was measured by counting in a gamma counter. The results are shown in FIG. 1.

Example 2

Preparation of Liposomes

Cationic lipid-oligonucleotide particles were prepared using the procedure of Example 1 by dissolving 50 μg of a 21-residue oligonucleotide in distilled, deionized water. 0.5 μmoles DOTAP was dissolved in chloroform, and the oligonucleotide was extracted into the chloroform according to Example 1.

Following the extraction, phosphatidylcholine (PC, iodine number 40) and cholesterol in a 2:1 ratio (PC:chol) were added to the chloroform organic phase containing the oligonucleotide-cationic lipid particles. Typically, the amount of PC added was 0.5 μmoles, 1.0 μmoles or 2.0 μmoles. After addition of the neutral lipids, 0.2 mL of distilled deionized H$_2$O was added and the mixture sonicated briefly to emulsify the mixture. The organic phase was evaporated in a Roto-vap under a vacuum of 500–700 mmHg. Liposomes formed once the system reverted into the aqueous phase. The liposomes were typically between 200 and 400 nm in diameter.

Example 3

Encapsulation Efficiency of Polynucleotide

A suspension of liposomes was prepared according to Example 2, with the addition of a trace amount of $^{125}$I labelled oligonucleotide (prepared as in Example 1). The encapsulation efficiency and oligonucleotide:phospholipid ratio was determined as follows.

The encapsulation efficiency was determined by separating the non-entrapped 21-mer oligonucleotide from the liposome-associated oligonucleotide on a metrizamide gradient and measuring by gamma counter the amount of oligonucleotide in each fraction. The encapsulation efficiency was taken as the counts in the liposome-associated oligonucleotide fraction over the total number of counts measured.

The metrizamide gradient was performed as follows. A 20% metrizamide/10% metrizamide/deionized $H_2O$ gradient was set in 12 mL centrifuge tubes by sequentially layering 1.5 mL of 20% metrizamide, 8 mL of 10% metrizamide and 2 mL of deionized $H_2O$. A control experiment of free oligonucleotide verified that 100% of free, non-lipid associated oligonucleotide remained in the 20% metrizamide fraction.

The liposome samples were placed on the gradient column and the gradients were then centrifuged at 240,000×g for 4 hours at 4° C. After centrifugation, a lipid band at the 10% metrizamide/deionized $H_2O$ interface was visible. The lipid was collected from the 10% metrizamide/$H_2O$ interface by aspiration with a pipette and counted in a gamma counter and then assayed for phosphate content. Table 1 gives the results from for three liposomal formulations containing 0.5, 1.0 or 2.0 μmoles phosphatidylcholine.

Example 4

Liposomes with a Surface-Coating of Polyethylene Glycol

Liposomes having a surface coating of polyethylene glycol (PEG) were prepared according to the procedure described in Example 2 by extracting 50 μg of oligonucleotide with a trace of $^{125}$I-oligonucleotide in deionized water with 0.5 μmoles DOTAP in chloroform. Then, 3 μmoles of phosphatidylcholine (PC40), 1.75 μmoles of cholesterol, and 0.175 μmoles of distearoyl phosphatidylethanolamine derivatized with PEG (mPEG$_{2000}$-DSPE) (PC:Chol:mPEG molar ratio of 2:1:0.1) were added to the organic lipid phase, containing 0.5 μmoles of DOTAP and the extracted oligonucleotide. A trace of $^3$H-Chol was also added to the organic phase.

Liposomes were prepared from this mixture by evaporation of the chloroform and 200 μL deionized $H_2O$ was added to increase the volume for extrusion. The liposome suspension was extruded through 400 nm and 200 nm polycarbonate filters to diameters below 200 nm.

The liposome suspension was characterized by separation of the non-entrapped oligonucleotide from the lipid-associated oligonucleotide on a metrizamide gradient as described in Example 3, except for a 12 hour centrifugation time. After centrifugation, the gradients were fractioned carefully by making a small hole in the bottom of the centrifugation tube and collecting the phases in equal drop fractions in scintillation vials. Both γ (for $^{125}$I-oligonucleotide) and β (for $^3$H-Chol) counts were measured, then β counts for each fraction were corrected for the γ signal. FIG. 3 gives a representative gradient profile and the results are summarized in Table 2.

Example 5

Preparation of Liposomes for in vivo studies
A. Preparation of Comparative Neutral Liposomes Neutral liposomes encapsulating an 18-mer antisense oligodeoxynucleotide were prepared by hydrating a lipid film in a concentrated solution of the oligonucleotide. Partially hydrogenated soy phosphatidylcholine (PC40), cholesterol and polyethylene glycol distearoyl phosphatidylethanolamine (PEG$_{2000}$-DSPE) were mixed in chloroform at a molar ratio of 2:1:0.1. The mixture was dried to a thin film by rotary evaporation and then traces of chloroform were removed under vacuum overnight. A solution of 1.7 mM oligonucleotide was added to the lipid film to give a phospholipid concentration of approximately 300 mM, the film was allowed to hydrate for six hours at room temperature. An equal volume of oligonucleotide solution was then added and the tube was vortexed for approximately on minute. Next, the mixture was diluted to 75 mM phospholipid with Hepes buffer (25 mM Hepes, 140 mM NaCl, pH7.4) and sonicated for 2 minutes. The liposomes were then extruded under $N_2$ pressure through a 200 nm Nucleopore polycarbonate filter in Hepes buffer according to Olson et al. (Olson, F., Biochim. Biophys. Acta 557:9–23 (1979)). Liposomes were sized by dynamic light scattering using a Brookhaven B190 particle sizer (Brookhaven Instrument, Holtsville, N.Y.). Free oligonucleotide was separated from lipid associated oligonucleotide by filtration down a Sepharose CL-4B (Pharmacia, Sweden) column equilibrated with Hepes buffer.

B. Preparation of Cationic Liposomes Having a Surface Coating of PEG

1. Preparation of $^{32}$P-labelled oligonucleotide. An 18-mer phosphorothioate oligonucleotide complementary to the MDRI gene was synthesized by the University Core DNA Services Lab at the University of Calgary (Calgary, AB). A $^{32}$P-labelled oligonucleotide was prepared following the general procedure of Sambrook et al. (Sambrook, J. et al. (1989) Molecular Cloning: A Laboratory Manual, Cold Spring Harbor Laboratory Press, New York.)

Briefly, 100 ng oligonucleotide was mixed with 50 μCi $^{32}$P-γ-ATP (ICN Pharamaceuticals, Inc., Irvine, Calif.), 5×'s forward reaction buffer and 10 units T4 kinase (Gibco BRL, Gaithersburg, Md.) to a total volume of 20 μL. The mixture was incubated at 37° C. in a water bath for 45 minutes. Following incubation, 80 μL buffer (10 mM Tris, 1 mM EDTA) was added and then the oligonucleotide was extracted using phenol/chloroform/isoamyl alcohol (25:24:1) (FisherBiotech, Fair Lawn, N.J.). Free $^{32}$P-γ-ATP was removed by separation on a Sephadex G-50 (Pharmacia, Sweden) spin column.

2. Liposome Preparation. The cationic lipid 1,2-Dioleoyl-3-trimethyl ammonium-propane (DOTAP) (Avanti Polar Lipids, Alabaster, Ala.) was used to exact the 18-mer phosphorothioate oligonucleotide through a Bligh and Dyer monophase. Up to 700 μg (approximately 0.118 μmoles) of 18-mer oligonucleotide was diluted in 250 μL double distilled $H_2O$ plus a trace of $^{125}$I- or $^{32}$P-labelled oligonucleotide. In a separate tube, up to two μmoles of DOTAP were diluted to 250 μL in CHCl$_3$ and 510 μL of MeOH was added. The oligonucleotide in double distilled $H_2O$ was then added to the CHCl$_3$/MeOH mixture containing DOTAP and the sample was mixed to form a monophase. Following 30 minutes incubation at room temperature, 250 μL of CHCl$_3$ were added, followed by 250 μL of double distilled $H_2O$. The tube was vortexed briefly and then centrifuged at 900×g for 7 minutes. The system then existed as a biphase and the upper, aqueous phase, was removed and the amount of oligonucleotide was determined either by radioactive counts or by measuring the absorbance at 260 nm. This procedure resulted in ~95% of the oligonucleotide being extracted into the organic phase when a 1:1 (+/−) charge ratio was used (DOTAP:oligonucleotide).

Next, partially hydrogenated soy phosphatidylcholine (PC40), cholesterol and mPEG-DSPE (all in CHCl$_3$) were added to the organic phase to give a molar ratio PC40:Chol:DOTAP:mPEG-DSPE of 3:2:1:0.2. Following transfer into a glass test tube, enough double distilled $H_2O$ was added so that the phospholipid concentration would be 20–30 mM in $H_2O$ and the emulsion was vortexed and then sonicated for approximately one minute. The organic phase was then evaporated off under rotary evaporation at approximately 400 mmHg. The system formed a gel phase following the evaporation of most of the organic phase and following further evaporation (sometimes with slight agitation), the system reverted into the aqueous phase which was briefly vortexed and then further evaporated. The vesicles formed by this procedure had a diameter in the range of 600 to 800 nm which were subsequently extruded through 400 and then 200 nm polycarbonate filers.

Liposomes were sized by dynamic light scattering using a Brookhaven BI90 particle sizer (Brookhaven Instrument, Holtsville, N.Y.). The neutral liposomes had an average diameter of 197±2 nm (polydispersity 0.032±0.012) while the DOTAP cationic liposomes had an average diameter of 188±1 nm (polydispersity 0.138±0.018). The size was stable in buffer at 4° C. as well as in 25% FBS at 37° C. for at least three days (data not shown).

Free oligonucleotide was separated from lipid-associated oligonucleotide by filtration down a Sepharose CL-4B (Pharmacia, Sweden) column equilibrated with Hepes buffer. The fractionation profiles for the cationic liposomes and the neutral liposomes are shown in FIGS. 4A and 4B, respectively.

Example 6

In vivo Administration of the Liposomes

Female ICR outbread mice (6–8 weeks old) were purchased from Charles River and used within 5 weeks of delivery at which time the weight ranged from 24 to 30 grams. Mice were given a single bolus injection via the tail vein of 0.2 mL of liposomes at a lipid dose of 0.5 μmoles phospholipid per mouse. Radioactive counts from each injection ranged from 0.4 to $2 \times 10^5$ cpm. At specific time points (0.25, 0.5, 1, 4, 12, 24 hours) mice (3 per group) were sacrificed, and organs were dissected, weighed, and radioactive counts determined in a Beckman gamma 8000 counter. Liver, spleen, lung, heart, kidney, 100 μL blood, and thyroid were dissected and counted, and the remainder of the animal (carcass) was also counted. The radioactive counts in each tissue and the carcass were corrected using blood correction factors which were previously determined, (Allen, T. M., U.C.L.A. Symposium on Molecular and Cellular Biology, in Lopez-Berestein, G. and Fidler, I., eds. 89:405–415, Alan R. Liss, New York). Blood counts were extrapolated to the total blood volume of the mouse.

The results for the in vivo administration are shown in FIGS. 5, 6 and 7.

Although the invention has been described with respect to particular embodiments, it will be apparent to those skilled in the art that various changes and modifications can be made without departing from the invention.

What is claimed is:

1. A liposome composition for in vivo administration of a polynucleotide, comprising
   an aqueous suspension of liposomes composed predominantly of liposomes having an inner coating of cationic vesicle-forming lipids which surround a polynucleotide, said inner coating surrounded by an outer coating of neutral vesicle-forming lipids, said liposomes being formed by removing an organic solvent from an emulsion composed of polynucleotide-cationic lipid particles and neutral vesicle-forming lipids in a non-ionic aqueous solvent and the organic solvent.

2. The composition of claim 1, wherein said polynucleotide is selected from the group consisting of DNA, RNA, and fragments and analogs thereof.

3. The composition of claim 1, wherein said polynucleotide is an antisense oligonucleotide.

4. The composition of claim 1, wherein said cationic lipid is selected from the group consisting of 1,2-dioleoyloxy-3-(trimethylamino) propane (DOTAP); N-[1-(2,3,-ditetradecyloxy)propyl]-N,N-dimethyl-N-hydroxyethylamimonium bromide (DMRIE); N-[1-(2,3,-dioleyloxy)propyl]-N,N-dimethyl-N-hydroxyethylammoniumbromide(DORIE); N-[1-(2,3-dioleyloxy) propyl]-N,N,N-trimethylammonium chloride (DOTMA); 3β[N-(N', N'-dimethylaminoethane) carbamoly] cholesterol (DC-Chol); and dimethyldioctadecylammonium (DDAB).

5. The composition of claim 1, wherein said neutral vesicle-forming lipid is a phospholipid.

6. The composition of claim 1, wherein said liposomes further include a neutral lipid derivatized with a hydrophilic polymer to form a surface coating of hydrophilic polymer chains.

7. The composition of claim 1, wherein said liposomes have a size between about 50–300 nm.

8. The composition of claim 1, wherein said liposomes further include a ligand for targeting to a selected site.

9. The composition of claim 6, wherein said hydrophilic polymer is polyethylene glycol.

10. A liposome composition for in vivo administration of a polynucleotide, comprising
    an aqueous suspension of liposomes formed by (a) preparing polynucleotide-cationic lipid particles in an organic solvent and (b) mixing the particles with neutral vesicle-forming lipids in the presence of a non-ionic aqueous solvent to form an emulsion and (c) removing the organic solvent from the emulsion to form liposomes having (i) an outer coating of the neutral vesicle-forming lipid and an inner coating of a cationic vesicle-forming lipid, (ii) a central core with an inner surface, and (iii) the polynucleotide entrapped in the central core and localized predominantly on the inner surface.

11. The composition of claim 10, wherein said polynucleotide is selected from the group consisting of DNA, RNA, and fragments thereof.

12. The composition of claim 10, wherein said polynucleotide is an antisense oligonucleotide.

13. The composition of claim 10, wherein said liposomes further include a neutral lipid derivatized with a hydrophilic polymer to form a surface coating of hydrophilic polymer chains.

14. The composition of claim 10, wherein said liposomes have a size between about 50–300 nm.

15. The composition of claim 10, wherein said liposomes further include a ligand for targeting to a selected site.

16. The composition of claim 13, wherein said hydrophilic polymer is polyethylene glycol.

17. A method of entrapping a polynucleotide in liposomes, comprising
    forming polynucleotide-cationic lipid particles in a lipid solvent suitable for solubilization of the cationic lipid by (i) dissolving the polynucleotide in a non-ionic solvent which is immiscible with the lipid solvent; (ii) contacting the polynucleotide with a charge-neutralizing amount of cationic lipid solubilized in the lipid solvent in the presence of a third solvent effective to form a single phase solvent system; (iii) adding additional non-ionic solvent or lipid solvent to the single phase system under conditions effective to form a two-phase system; and (iv) removing the non-ionic solvent phase, adding neutral vesicle-forming lipids and a non-ionic aqueous solvent to the lipid solvent containing said particles to form an emulsion, and evaporating the lipid solvent to form liposomes having the polynucleotide entrapped therein.

18. The method of claim 17, wherein said evaporating further includes hydrating with an aqueous medium.

19. A method of administering a polynucleotide to a subject, comprising preparing a suspension of liposomes composed predominantly of liposomes having an inner coating formed of cationic vesicle-forming lipids which surround a polynucleotide, said inner coating being surrounded by an outer coating formed of neutral vesicle-forming lipids, said liposomes being formed by removing an organic solvent from an emulsion composed of polynucleotide-cationic lipid particles and neutral vesicle-forming lipids in a non-ionic aqueous solvent and the organic solvent, and administering said liposomes to the subject.

20. The method of claim 19, wherein said administering is via intravenous administration.

21. The method of claim 19, wherein said preparing includes preparing a suspension of liposomes including a polynucleotide selected from the group consisting of antisense oligonucleotides, DNA, RNA, and fragments and analogs thereof.

22. The method of claim 19, wherein said preparing includes preparing liposomes having a surface coating of a hydrophilic polymer by including a neutral lipid derivatized with said hydrophilic polymer.

* * * * *